United States Patent
Chen

(10) Patent No.: US 9,119,987 B2
(45) Date of Patent: Sep. 1, 2015

(54) PERSONALIZED EXERCISE SIMULATION SYSTEM

(71) Applicant: Bion Inc., New Taipei (TW)

(72) Inventor: Yu-Yu Chen, New Taipei (TW)

(73) Assignee: Bion Inc., New Taipei (TW)

( * ) Notice: Subject to any disclaimer, the term of this patent is extended or adjusted under 35 U.S.C. 154(b) by 0 days.

(21) Appl. No.: 14/583,756

(22) Filed: Dec. 28, 2014

(65) Prior Publication Data

US 2015/0182799 A1 Jul. 2, 2015

(30) Foreign Application Priority Data

Dec. 30, 2013 (TW) .............................. 102148948 A

(51) Int. Cl.
*A63B 24/00* (2006.01)
*A61B 5/11* (2006.01)

(52) U.S. Cl.
CPC .............. *A63B 24/0087* (2013.01); *A61B 5/11* (2013.01); *A63B 24/0062* (2013.01)

(58) Field of Classification Search
CPC .............. A63B 24/00; A63B 24/0062; A63B 24/0087; A61B 5/11

See application file for complete search history.

(56) References Cited

U.S. PATENT DOCUMENTS

| 8,463,573 B2 * | 6/2013 | Flentov et al. ................ 702/141 |
| 8,465,397 B2 * | 6/2013 | Saalasti et al. .................... 482/9 |
| 8,740,751 B2 * | 6/2014 | Shum ................................ 482/8 |

* cited by examiner

*Primary Examiner* — Glenn Richman
(74) *Attorney, Agent, or Firm* — Bruce Stone LLP; Joseph A. Bruce

(57) ABSTRACT

The present application is provided a personalized exercise simulation system. The system includes a microprocessor, an equipment adjustment unit, a displayer, a reality controlling parameter transmitting port, a reality controlling parameter unit, a reality image unit, a path trajectory data memory, a displayer, a controlling instruction outputting port. The microprocessor acquires a path coordinate, path parameter from the reality controlling parameter unit and an equipment adjustment instruction produced by the equipment adjustment unit. Then the processor outputs the instruction to the exercise device by the outputting port to adjust one of speed, gradient, or resistance of the exercise device. Meanwhile, the microprocessor acquires a reality image corresponded to the path coordinate from the reality image unit, and then display the reality image on the displayer. The present application further includes one of a camera device, a position system, or one piece of map information.

10 Claims, 11 Drawing Sheets

PERSONALIZED EXERCISE SIMULATION SYSTEM

PRIORITY

This application claims priority benefit of Taiwan Patent Application Ser. No. 102148948 filed 2013 Dec. 30 which is hereby incorporated herein by reference its entirety.

BACKGROUND OF THE INVENTION

1. Field of the invention

The present application relates to a exercise device. More particularly, the present application relates to a personalized exercise simulation system.

2. Description of the prior art

Current people always choose the warming season to do outdoor exercise (e.g. jogging, riding), and choose hot weather or cold weather to do indoor exercise.

For the people who love exercise, the applying device or pattern of both exercise are very similar. For example, most of people loved outdoor jogging prefer the treadmill for indoor exercise, vice versa people loved outdoor riding prefer the stationary bike for indoor exercise.

Choosing the proper exercise device is a basic requirement for exercise trainer, and providing people enjoy the pleasure and efficiency of outdoor exercise when comes to indoor environment is a important issue.

CCD, GPS, high capacity memory, outdoor watch is able to acquire user's data, path, and image. Allows the user to read, analysis or compare with the virtual reality image when doing the indoor exercise.

Current virtual reality device of indoor exercise still use the template image file or 3-D image yet cannot simulate the reality image according to the user's habit, path, altitude, and cannot operate in coordination with the speed state, heartbeat state . . . etc when user exercising in the outdoor environment.

SUMMARY OF THE INVENTION

To achieve the aforementioned objective, the present application provides a outdoor exercise device which can acquire real time image and coordinate along the exercise path of user's scheduled path, and record speed, distance, altitude, gradient, and heartbeat, blood pressure, temperature parameter of exercise state.

When the user operates the indoor exercise device such as indoor bicycle trainer, indoor stationary bike or treadmill, the present application can download the outdoor image, position, speed, a real time body information of user to the displayer of indoor exercise device by a transmitting interface and reappear the outdoor reality image, exercise environment and body state.

In the preferred embodiment, while user configures a camera device when he go out to exercise, the camera lens and the position system of the camera device stores the parameter of the exercise path. When the user finish the aforementioned exercise path, the device will transmits the reality image captured by the camera device, gradient parameter, altitude parameter, path direction parameter, speed parameter to the exercise simulation controlling device. The exercise simulation controlling device can transmit the aforementioned parameter to the exercise device, and enable the exercise device to adjust the exercise speed, gradient, resistance according to the aforementioned parameter, and provides the user with the reality experience.

The present application can control exercise device by the position parameter, gradient parameter, altitude parameter acquired in outdoor exercise, and provide the user compare or compete with the last time exercise after finish the this time exercise.

The following embodiment and the drawing thereof will further illustrate the specific embodiment of present application.

DETAILED DESCRIPTION OF THE PREFERRED EMBODIMENT

To express the technical features, contents, advantages and effects of the present application to assist examiner in understanding the present application, the specification and drawings are expressed in embodiments as followed. The drawings are provided to exemplarily show the present application and may not show the true ratio and arrangement of the present application. The drawings are not intended to limit the scope of the present application with the ratio and arrangement thereof.

Figure 1:
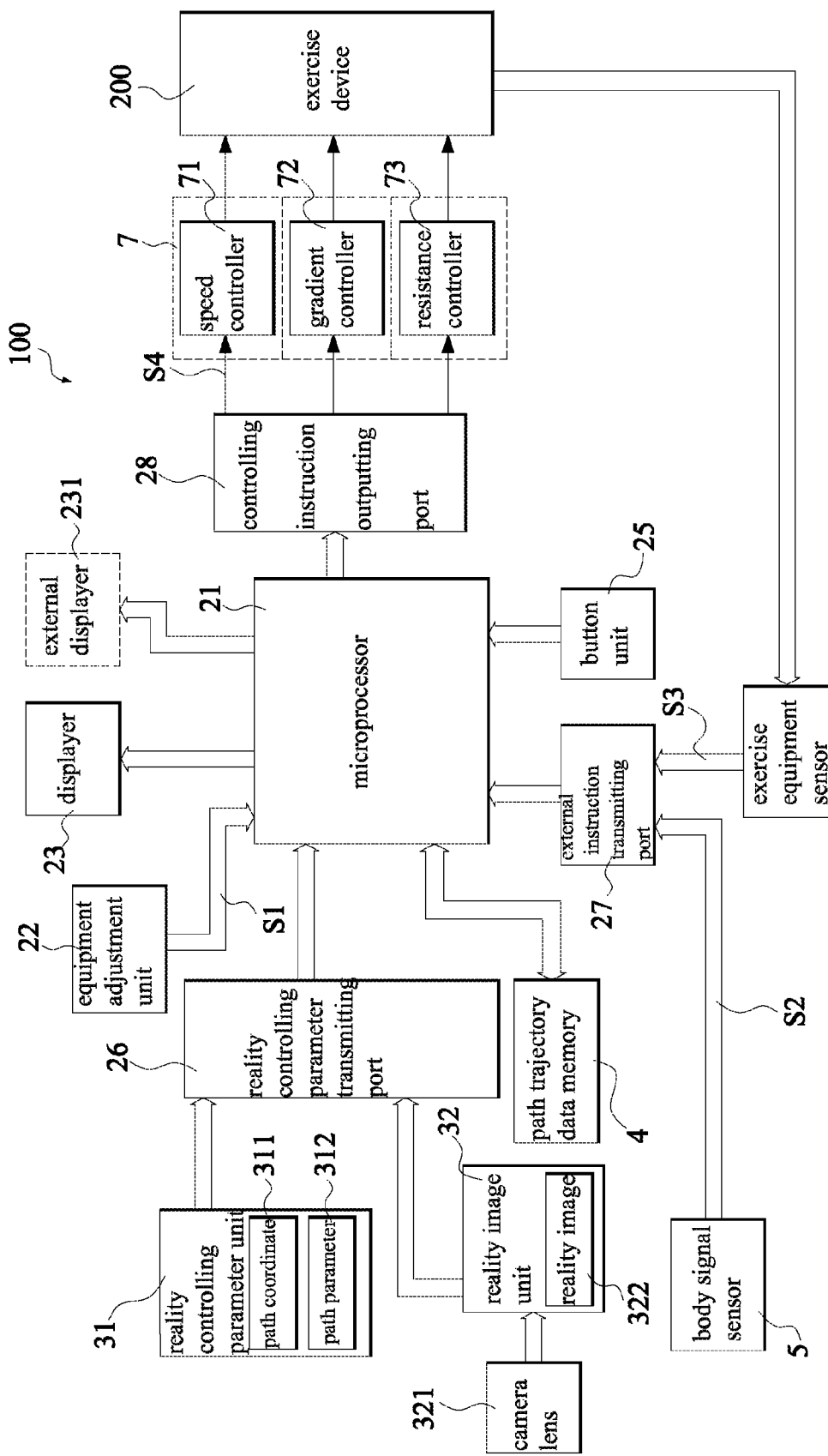
FIG. 1 shows the circuit block diagram of first embodiment of exercise simulation controlling device of present application.

FIG. 1 shows a circuit block diagram of first embodiment of personalized simulation system of present application. The system comprises a exercise simulation controlling device 100 connected with an exercise device 200. The exercise simulation controlling device 100 comprises a microprocessor 21, a equipment adjustment unit 22, a displayer 23, an external displayer 231, a button unit 25, a reality controlling parameter transmitting port 26, an external instruction transmitting port 27, a controlling instruction outputting port 28.

The microprocessor 21 connects with the displayer 23 and selected to connect the external displayer 231. The equipment adjustment unit 22 is capability to generate at least one piece of equipment adjustment instruction S1 to the microprocessor 21. The button unit 25 is provided the user to insert date.

The reality controlling parameter unit 31 connects with the realty controlling parameter transmitting port 26. The reality controlling parameter unit 31 stores at least one path coordinate 311 and a path parameter 312 of selected path. Each path coordinate 311 stores a coordinate parameter of selected path. The path parameter 312 comprises a direction parameter, altitude parameter, gradient parameter, coordinate parameter, time parameter of selected path.

The reality image unit 32 connects with reality controlling parameter transmitting port 26. The camera lens 321 connects to the reality image unit 32, captures the reality image, and stores at least one reality image 322 in reality image unit 32. Wherein the reality image 322 is corresponding to the path coordinate 311.

The path trajectory data memory 4 connects with the microprocessor 21 and configured to store at least one piece of path trajectory data.

The external instruction transmitting port 27 connects the microprocessor 21, and transmits the sensed body information S2 to the microprocessor 21.

Controlling instruction outputting port 28 connects with the microprocessor 21, and connects with an exercise device 200 by an exercise equipment device controlling interface 7. And the exercise equipment controlling interface 7 further comprises a speed controller 71, a gradient controller 72, and a resistance controller 73 and uses aforementioned controller to control exercise equipment information S3 (including speed, gradient, or resistance) of the exercise device 200. The exercise information S3 of exercise device 200 can be sensed by the exercise equipment sensor 6 and transmitted to the microprocessor 21 by the external instruction transmitting port 27.

Wherein the microprocessor 21 of the exercise simulation controlling device 100 acquires a path coordinate 311 and path parameter 312 of reality controlling parameter unit 31 and a equipment adjustment information S1 produced by the equipment adjustment unit 22, then transmits the equipment controlling instruction S4 to exercise device 200 by the controlling instruction outputting port 28 so as to adjust one of the speed, gradient, resistance of the exercise device 200. Meanwhile, the microprocessor 21 of exercise simulation controlling device 100 acquires a reality image 322 corresponding to the path coordinate 311 from the reality image unit 32, and displays the reality image on the display 23 or external display 231.

Figure 2:
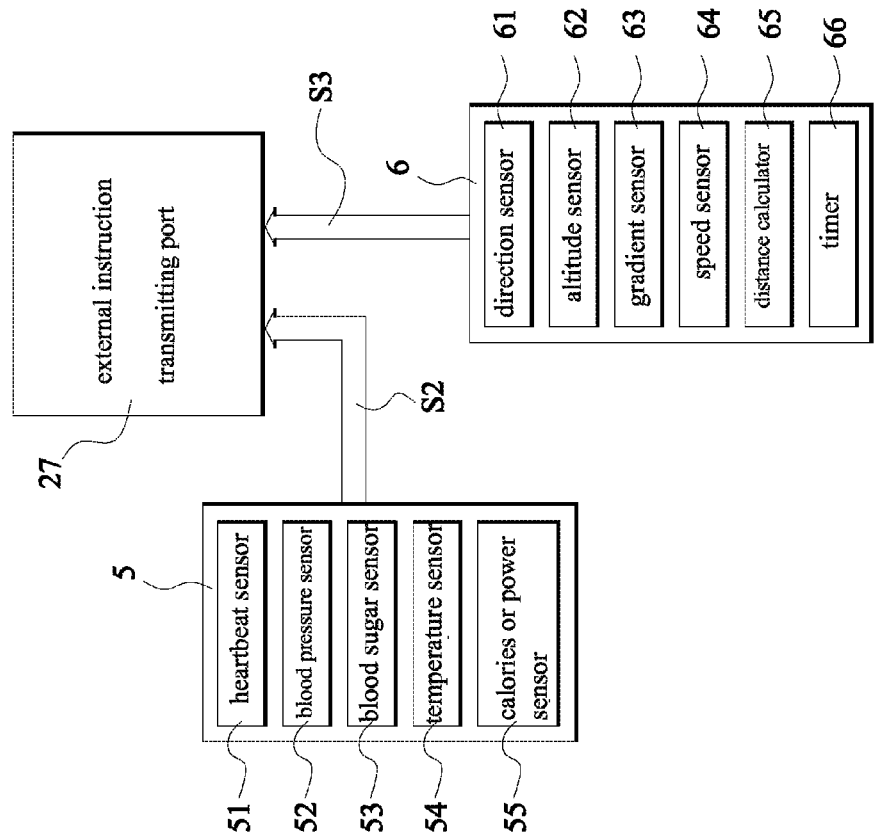
FIG. 2 shows the further embodiment of body signal sensor and exercise equipment sensor of FIG. 1.

FIG. 2 shows the further embodiment of body signal sensor and exercise equipment sensor of FIG. 1. Wherein the body signal sensor 5 is selected to comprise a heartbeat sensor 51, blood pressure sensor 52, blood sugar sensor 53, temperature sensor 54 and calories or power sensor 55, and configure these sensor to sense user's heartbeat, blood pressure, blood sugar, temperature, calories and power information respectively.

Exercise equipment sensor 6 further comprise a direction sensor 61, altitude sensor 62, gradient sensor 63, speed sensing 64, distance calculator 65, timer 65 to sense direction information, altitude information, gradient information, speed information, distance information, and timing information respectively.

Figure 3:
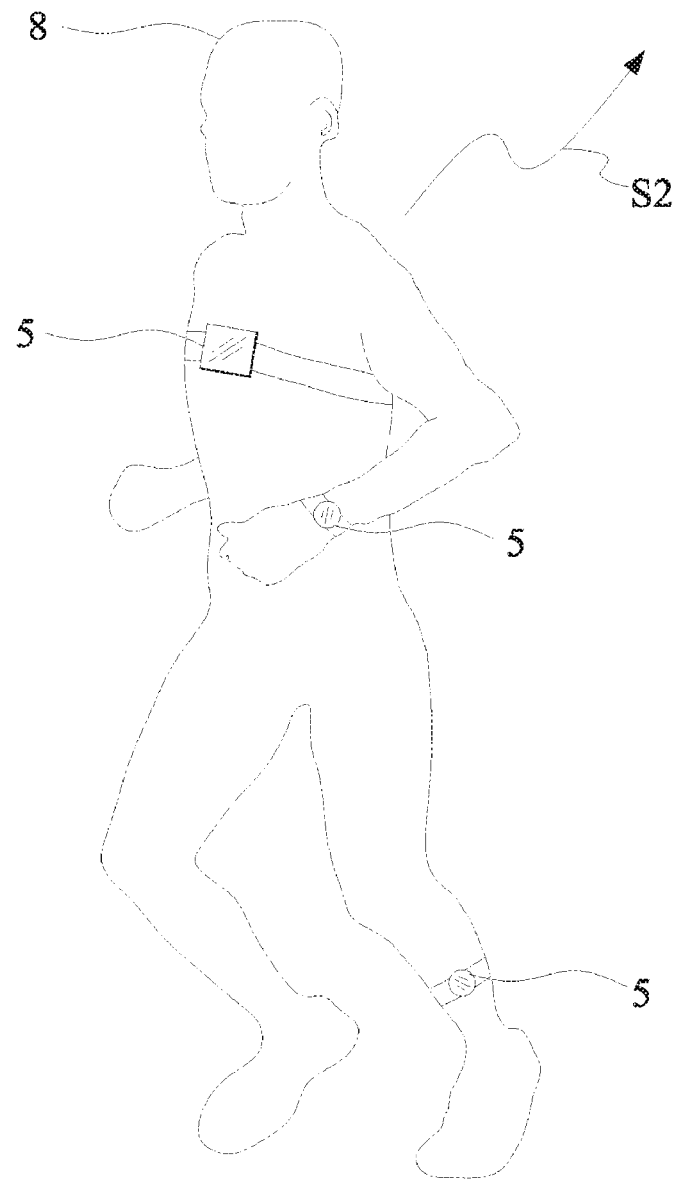
FIG. 3 shows the selected body portion of user which is configured body signal sensor.

FIG. 3 shows the selected body portion of user which is configured body signal sensor 5, and configures these sensor to sense at least one piece of body information of user.

Figure 4:
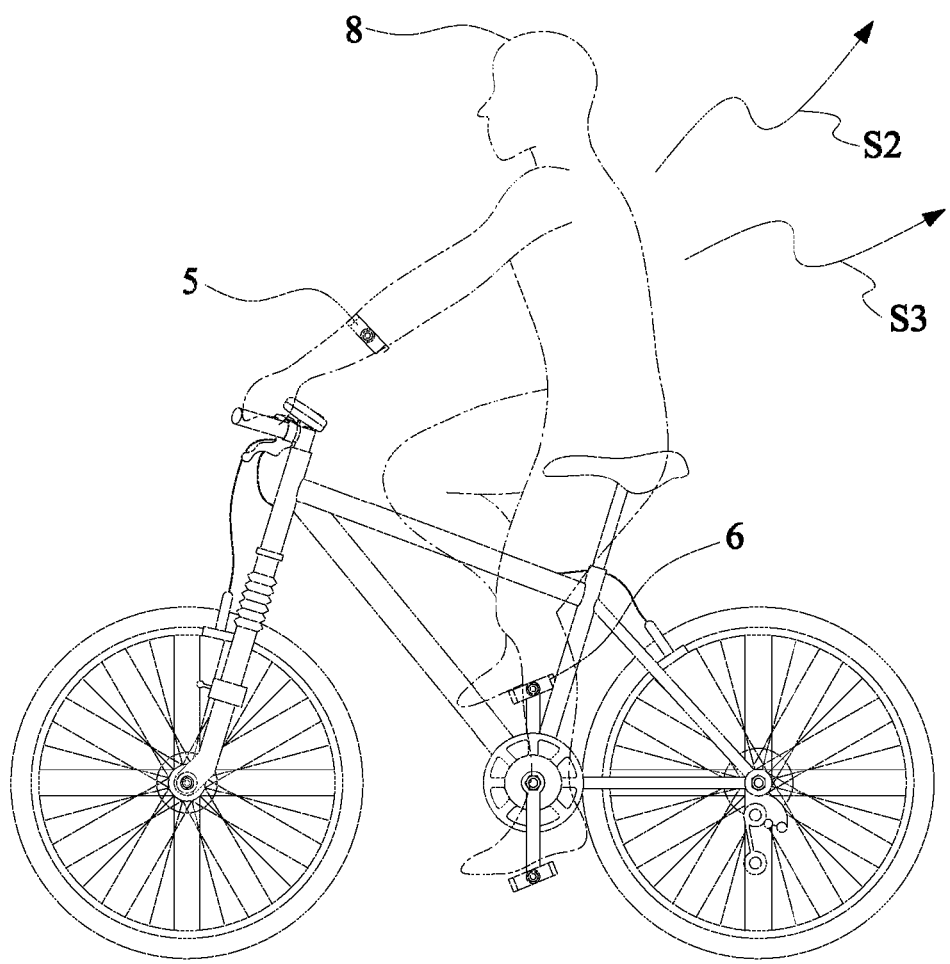
FIG. 4 shows a user configures body signal sensor when riding a bicycle and the exercise device configures a plurality of exercise equipment sensor.

FIG. 4 shows a user 8 configures body signal sensor 5 when operating an exercise device 200 (e.g. riding a bicycle) which provides at least one piece of body information S2 of user. The exercise device 200 configures multiple exercise equipment sensors 6, and produces exercise equipment information S3. When the application applies in a bicycle, the exercise equipment information S3 includes one of speed information, pedal speed information or power information.

Figure 5:
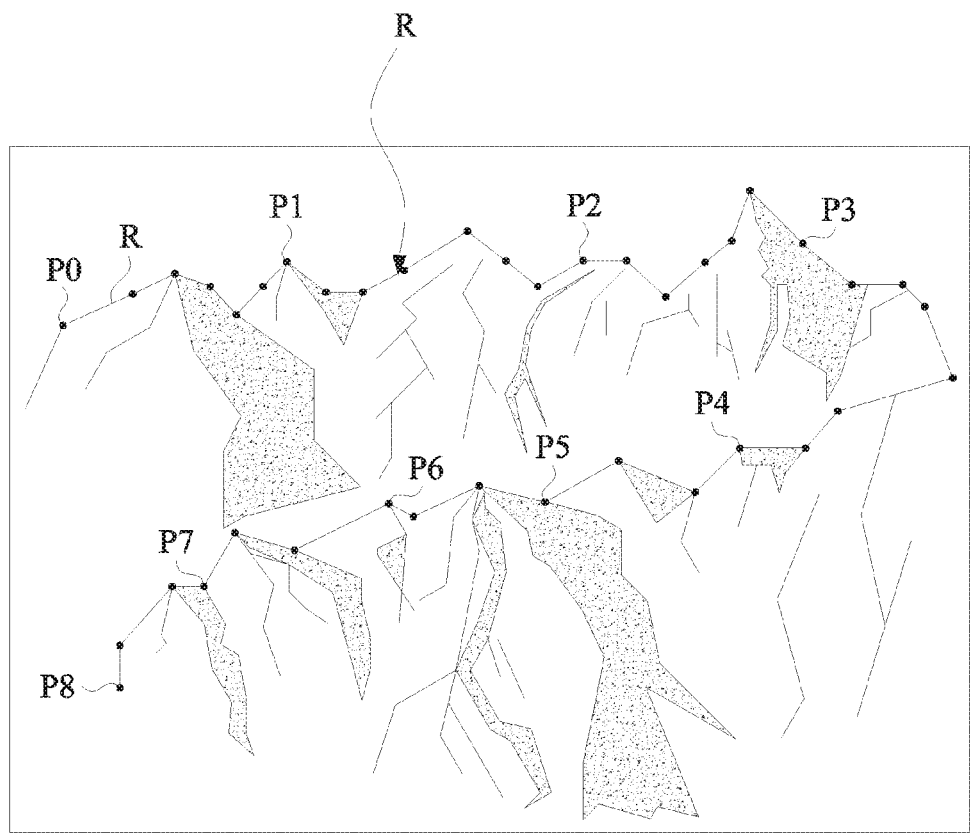
FIG. 5 shows an exercise path diagram which from an initial position to the target position and via a plurality of position.

Please referring FIG. 5, when user wears the exercise simulation controlling device 100 of present application, or configures the exercise simulation controlling device 100 on the riding bicycle along an exercise path R from an initial position P0 to a target position P1 and through a plurality of position P1~P7. Meanwhile, the device stores an exercise path R in the path trajectory data memory 4 by the sensor unit, stores the path coordinate 311 and path parameter 312 corresponded with each position P0~P8 respectively in the reality controlling parameter unit 31, and stores the reality image 332 in reality image unit 32.

When user finished the last time exercise path, the device stores the coordinate, path parameter, reality images captured by the camera device which are corresponding to the position P0~P8 of the exercise path R in the path trajectory data memory 4, so as to provide the device to operate the exercise device 200.

When the user operates the second exercise, the exercise simulation controlling device transmits the reality image to the displayer. The exercise simulation device transmits various coordinate, path parameter to the exercise device and adjusts exercise device's speed, gradient or resistance so as to provide the user with the reality experience.

Figure 6:
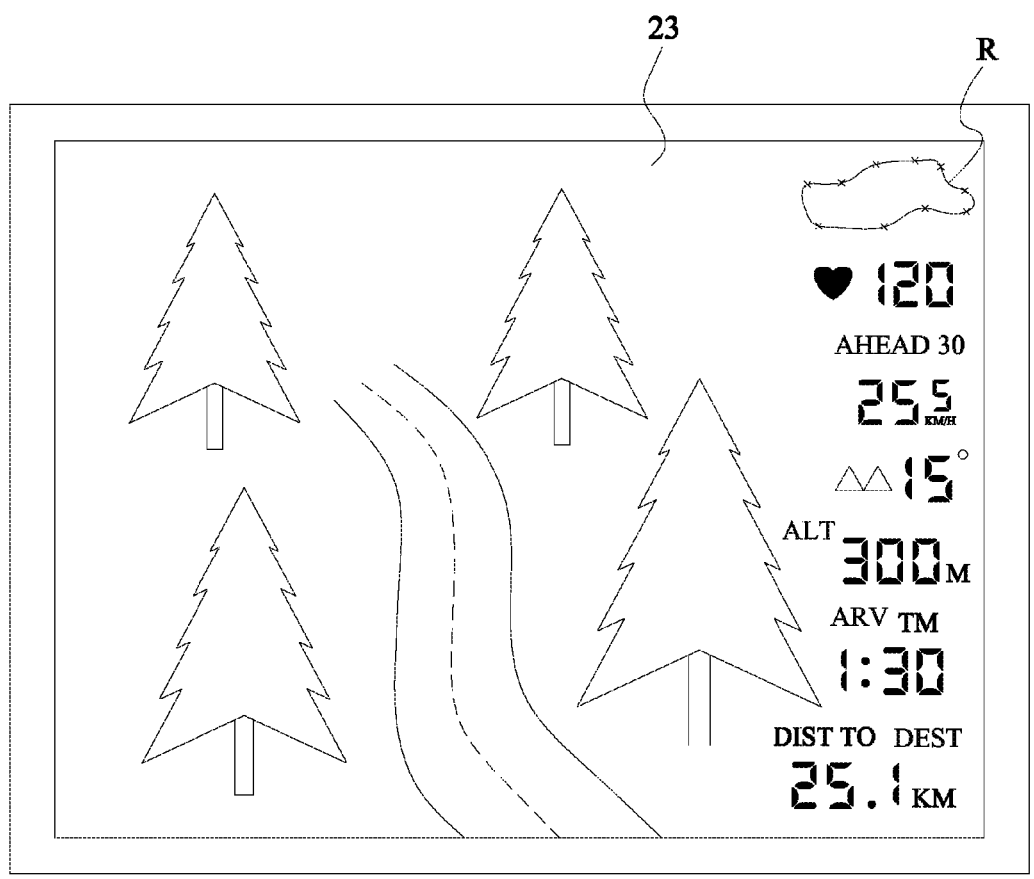
FIG. 6 shows a first schematic diagram of the displaying information displayed on the displayer and external displayer.

FIG. 6 shows a first schematic diagram of the displaying information displayed on the displayer 23 and external displayer 231. The display 23 and external displayer 231 display user's heartbeat information, direction parameter, altitude parameter, speed parameter, time parameter, distance parameter . . . , etc.

Figure 7:
FIG. 7 shows a second schematic diagram of the displaying information displayed on the displayer and external displayer.

FIG. 7 shows a second schematic diagram of the displaying information displayed on the displayer 23 and external displayer 231. The display 23 and external displayer 231 display user's heartbeat information, direction parameter, altitude parameter, speed parameter, time parameter, distance parameter . . . , etc.

Figure 8:
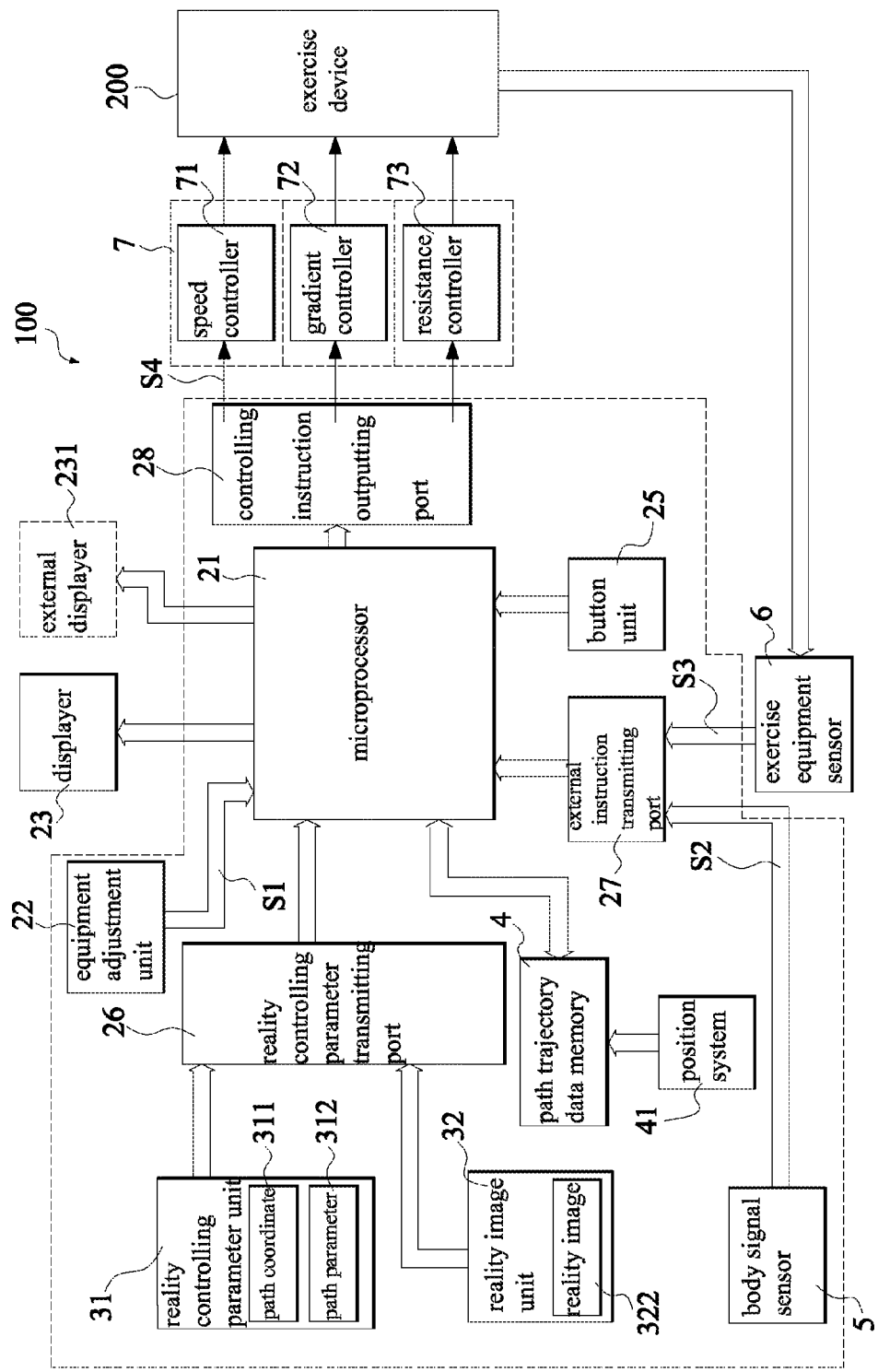
FIG. 8 shows the circuit bock diagram of second embodiment of exercise simulation controlling device of present application.

FIG. 8 shows the circuit bock diagram of second embodiment of exercise simulation controlling device of present application. The second embodiment is similar with the first embodiment, and the same device is labeled the same series number. In this embodiment, the path trajectory data memory 4 connects with a position system (e.g. GPS). The device acquires the coordinate, gradient, altitude, path and direction parameter of each position along the exercise path R, and stores these parameters in the path trajectory data memory 4.

Figure 9:
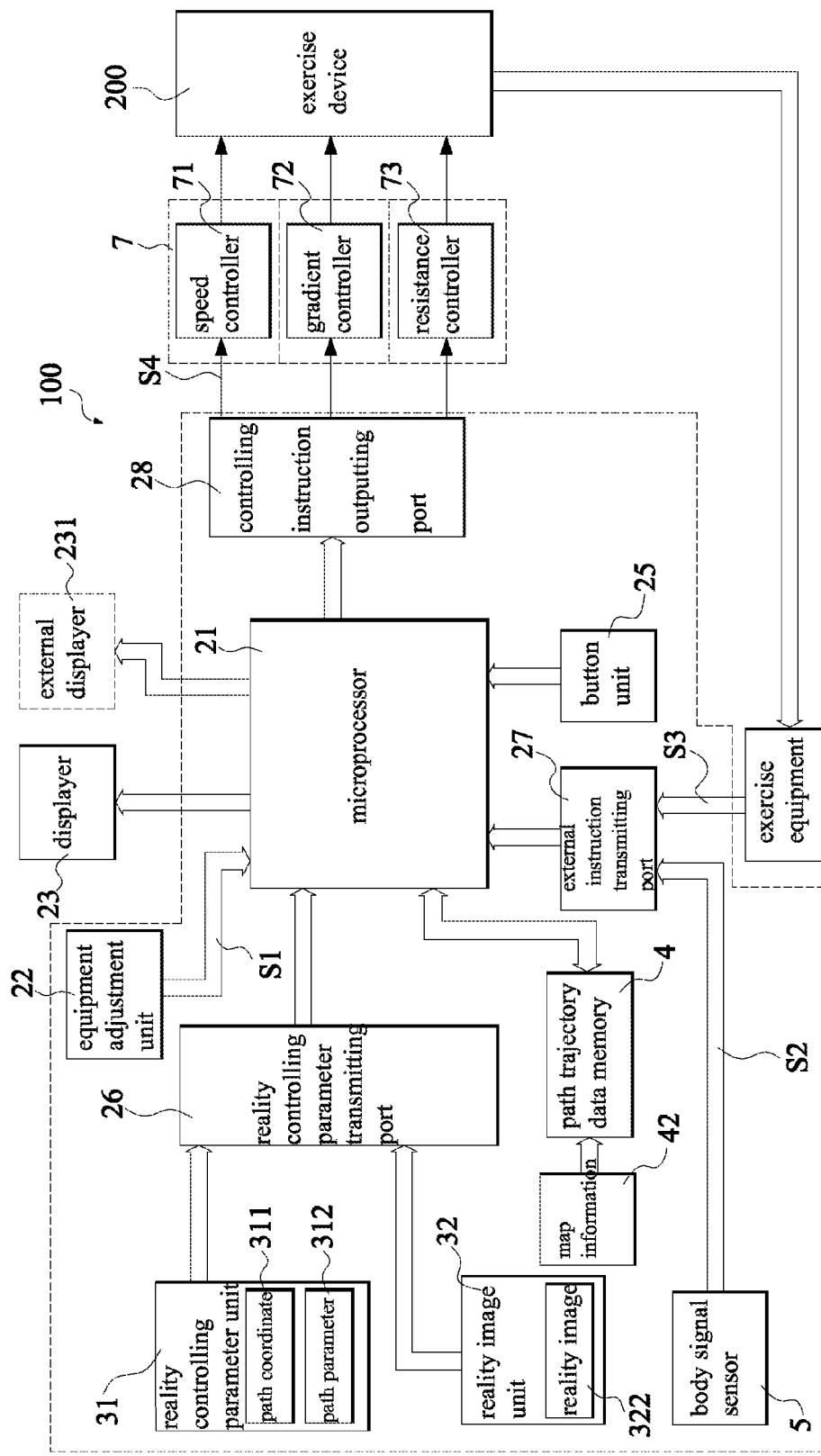
FIG. 9 shows the circuit block diagram of third embodiment of exercise simulation controlling device of present application.

FIG. 9 shows the circuit block diagram of third embodiment of exercise simulation controlling device of present application. The third embodiment is similar with the first embodiment, and the same device is labeled the same series number. In this embodiment, the path trajectory data memory 4 connects with a map information 42. The user can download the map image, gradient parameter, altitude parameter, path parameter and direction parameter . . . , etc from the internet (e.g. Google map™ or Google Earth™) as the map information 42, and stores there information in path trajectory data memory 4.

Figure 10:
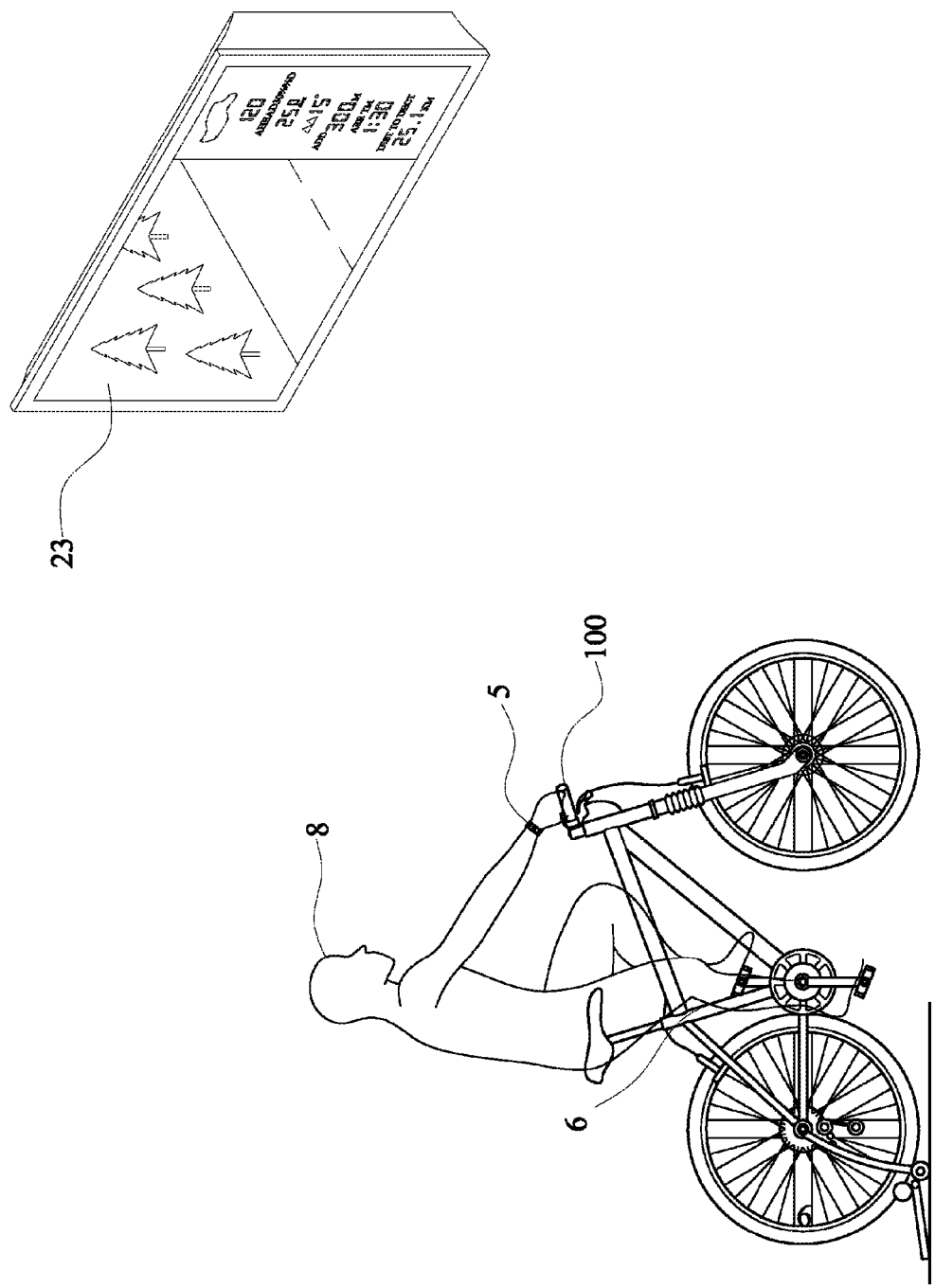
FIG. 10 shows one user uses the exercise simulation controlling device of present application.

FIG. 10 shows one user uses the exercise simulation controlling device of present application. When the user is exercising, the exercise simulation controlling device 100 of present application transmits the gradient parameter, altitude information, path parameter, direction parameter to the exercise device 200 to adjust and control the speed, gradient, resistance of exercise device 200 and transmit the reality image to the displayer 23.

Figure 11:
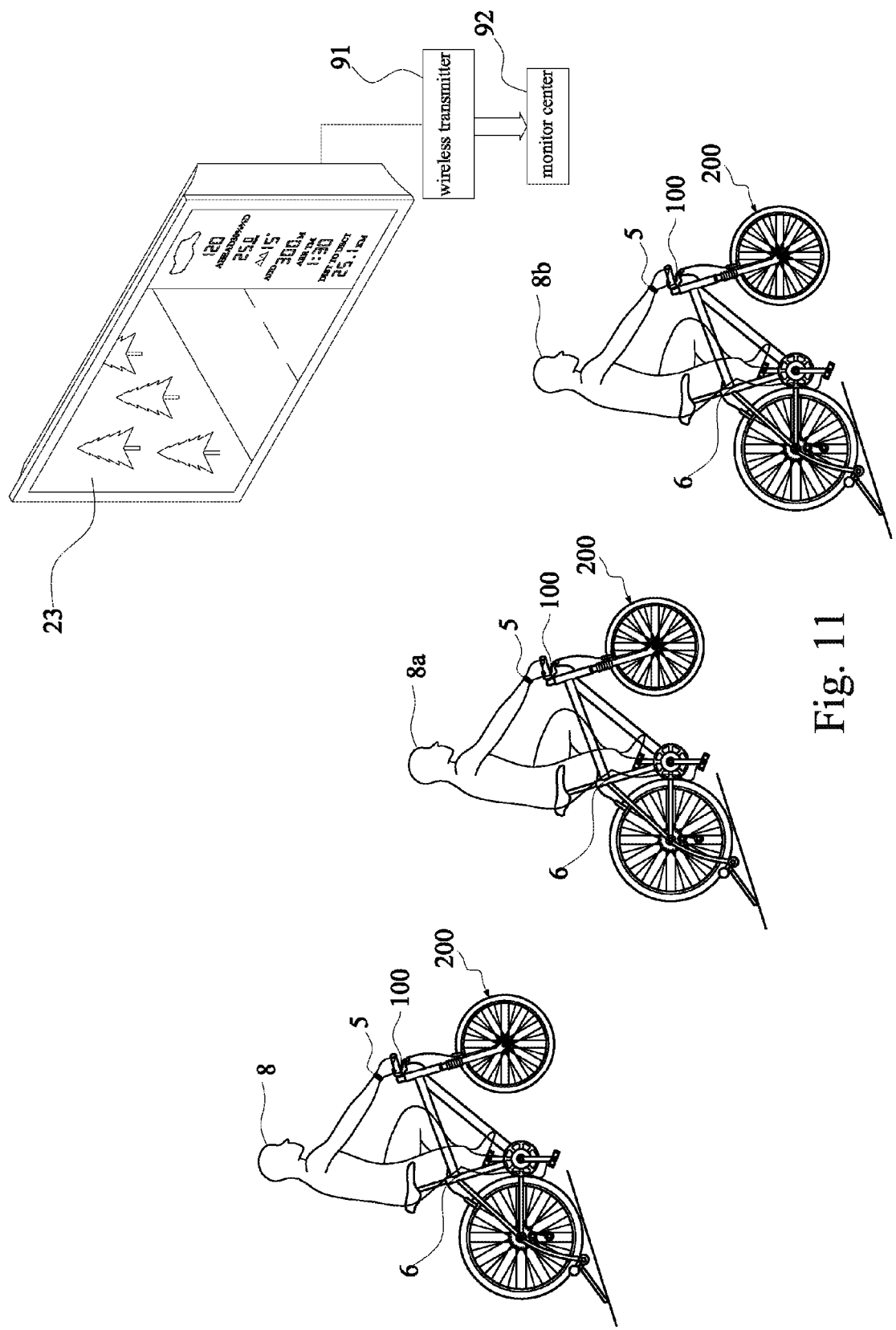
FIG. 11 shows multiple users use the exercise simulation controlling device of present application.

FIG. 11 shows the practical application of exercise simulation controlling device of this application. When at least one user 8, 8a, 8b is exercising, the exercise simulation controlling device of this application transmits the gradient parameter, altitude parameter, path parameter and direction parameter to the exercise 200 to adjust or control the speed, gradient, resistance of the exercise 200, and transmit the reality image to the displayer 23.

While in the exercising, the body information S2 of the plurality of user 8, 8a, 8b also can transmit to a monitor center 92 using the wireless means. And the monitor can monitor body information S2 of each user 8, 8a, 8b and exercising situation.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A personalized exercise simulation system, comprising an exercise simulation controlling device linked with an exercise device, the exercise simulation controlling device further comprising:
   a microprocessor;
   an equipment adjustment unit, producing at least one equipment adjustment instruction to the microprocessor;
   a displayer, connected with the microprocessor;
   a reality controlling parameter transmitting port, connected with the microprocessor;
   a reality controlling parameter unit, connected with the reality controlling parameter transmitting port, the reality controlling parameter unit further storing at least one path coordinate and a path parameter of a selected path, each of the path coordinate storing a coordinate parameter of the selected path, the path parameter comprising a direction parameter, an altitude parameter, a gradient parameter, or a speed parameter;
   a reality image unit, connected with the reality controlling parameter transmitting port, the reality image unit further storing at least one reality image, wherein the reality image correspond with the path coordinate;
   a path trajectory data memory, connected with the microprocessor and configured to store at least one piece of path trajectory data;
   an external displayer, connected with the microprocessor;
   a controlling instruction outputting port, connected with the microprocessor, and connected with the exercise device through an exercise equipment controlling interface;
   wherein, the microprocessor of the exercise simulation controlling device acquires the path coordinate and path parameter from the reality controlling parameter unit and the equipment adjustment instruction produced by the equipment adjustment unit, then transmits the controlling instruction to the exercise device thought the controlling instruction outputting port, and then adjusts one of speed, gradient and resistance of the exercise device;
   wherein, the microprocessor acquires the reality image from the corresponding path coordinate, and displays the reality image on the displayer or the external displayer.

2. The system as claimed in claim 1, further comprising an external instruction transmitting port connected with the microprocessor, wherein the external instruction transmitting port connects one of body signal sensor and exercise equipment sensor.

3. The system as claimed in claim 2, wherein the body signal sensor is configured to sense at least one piece of body information, and the exercise equipment sensor is configured to sense at least one piece of exercise equipment information of the exercise device.

4. The system as claimed in claim 3, wherein the piece of body information is selected from one piece of heartbeat information, one piece of blood pressure information, one piece of blood sugar information, one piece of temperature information, one piece of calorie information, or one piece of power information of a user.

5. The system as claimed in claim 3, wherein the piece of exercise equipment information is selected from one piece of bicycle speed information, one piece of pedal speed information, one piece of calorie information, or one piece of power information.

6. The system as claimed in claim 1, wherein the path parameter is selected from a direction parameter, an altitude parameter, a gradient parameter, a speed parameter, a coordinate parameter, or a time parameter of the path.

7. The system as claimed in claim 1, wherein the exercise equipment controlling interface further comprises a speed controller, a gradient controller, and a resistance controller.

8. The system as claimed in claim 1, further comprises a camera device connected with the path trajectory data memory.

9. The system as claimed in claim 1, further comprises a position system connected with the path trajectory data memory.

10. The system as claimed in claim 1, wherein the path trajectory data memory further connects with one piece of map information.

* * * * *